(12) United States Patent
Minion

(10) Patent No.: US 10,154,894 B2
(45) Date of Patent: Dec. 18, 2018

(54) ENDOGRAFTS FOR PARALLEL ENDOLUMINAL GRAFTS

(71) Applicant: David J. Minion, Lexington, KY (US)

(72) Inventor: David J. Minion, Lexington, KY (US)

(*) Notice: Subject to any disclaimer, the term of this patent is extended or adjusted under 35 U.S.C. 154(b) by 1686 days.

(21) Appl. No.: 13/655,078

(22) Filed: Oct. 18, 2012

(65) Prior Publication Data

US 2013/0103134 A1 Apr. 25, 2013

Related U.S. Application Data

(60) Provisional application No. 61/548,711, filed on Oct. 18, 2011.

(51) Int. Cl.
*A61F 2/07* (2013.01)
*A61F 2/06* (2013.01)
*A61F 2/954* (2013.01)

(52) U.S. Cl.
CPC .............. *A61F 2/07* (2013.01); *A61F 2/06* (2013.01); *A61F 2/954* (2013.01); *A61F 2002/061* (2013.01); *A61F 2230/0067* (2013.01); *A61F 2250/006* (2013.01); *A61F 2250/0039* (2013.01)

(58) Field of Classification Search
CPC ............... A61F 2/07; A61F 2/06; A61F 2/954
USPC ................................................. 623/11, 13, 35
See application file for complete search history.

(56) References Cited

U.S. PATENT DOCUMENTS

| | | | |
|---|---|---|---|
| 6,942,692 B2* | 9/2005 | Landau | A61F 2/07 623/1.27 |
| 2009/0177265 A1* | 7/2009 | Dierking | A61F 2/07 623/1.13 |
| 2009/0287145 A1* | 11/2009 | Cragg | A61F 2/07 604/96.01 |
| 2010/0305686 A1* | 12/2010 | Cragg | A61F 2/07 623/1.35 |

* cited by examiner

Primary Examiner — Vy Bui
(74) Attorney, Agent, or Firm — King & Schickli, PLLC

(57) ABSTRACT

An endograft is provided for a blood vessel having a branch extending from said blood vessel, including a body having a wall defining a lumen and an exterior surface. The endograft body includes a first portion defining or being made to define a non-circular cross-sectional dimension, and a second portion defining a circular cross-sectional dimension. Modular systems including the endograft and methods for creating endografts according to the disclosure are described also.

10 Claims, 5 Drawing Sheets

ENDOGRAFTS FOR PARALLEL ENDOLUMINAL GRAFTS

This utility patent application claims the benefit of priority in U.S. Provisional Patent Application Ser. No. 61/548,711, filed on Oct. 18, 2011, the entirety of the disclosure of which is incorporated herein by reference.

TECHNICAL FIELD

The invention relates to the design of endoluminal grafts, or endografts, which are medical devices designed to treat vascular pathology such as aneurysms or dissections. More specifically, the invention relates to parallel endoluminal grafts, i.e. multiple endografts placed side by side to allow preservation of blood flow in branch vessels that would otherwise need to be sacrificed in order to adequately treat vascular pathology such as aneurysms or dissections that involving or near such branches.

BACKGROUND OF THE INVENTION

Endoluminal grafts are intraluminal conduits that are generally comprised of a scaffolding (usually a metal stent) that is covered or lined with a fabric or graft material. As such, these are often termed "stent grafts." These conduits direct blood flow from one portion of the vasculature to another. The fabric portion provides containment of blood pressure within the conduit, thereby excluding the pressure from the vascular pathology (i.e., aneurysm or dissection A, see FIG. 1A) in which they are placed. Suitable materials and methods for fabricating such grafts, delivering them to their desired position in the body, and deploying them are well known in the art.

To be effective, endoluminal grafts must be deployed in a position where their proximal and distal ends provide an occlusive seal in a healthy portion of the blood vessel proximal and distal to the pathology being treated (FIG. 1B). These seal zones are critical for exclusion of the systemic blood pressure from the treated (diseased) segment such as aneurysm or dissection A.

In many instances, there are important branch vessels that originate in either the diseased segment or the seal zone (FIG. 2A) that would need to be sacrificed if the pathology were to be treated using a single standard endoluminal graft such as is shown in FIG. 1A. In contrast, the use of multiple endografts placed side by side in the seal zone can feasibly preserve flow in these important branch vessels while still excluding pressure from the diseased segment (FIG. 2B). This strategy has become an increasingly popular method for endovascular repair of aneurysms involving challenging anatomy such as branch vessels. In the art, it is commonly referred to as the "snorkel" or "chimney" technique. In most cases there is a larger main endograft used to treat the vascular pathology (usually in the aorta) and one or more smaller-diameter endografts (snorkels) placed alongside of it to preserve flow into the branch vessels (e.g., renal, mesenteric, or carotid arteries). In this manner, blood flow is preserved in these branch vessels that would otherwise have to be covered or excluded by the main endograft to achieve a good seal for exclusion of the diseased blood vessel segment.

However, one of the weaknesses of this technique is the imperfect nature of the seal inherent to the multiple side-by-side grafts. Conventional endografts typically define a circular cross-sectional dimension. Because each of the main endograft and snorkels define such a circular cross-sectional dimension, the snorkels interfere with the required occluding seal (see FIG. 1B for an illustration of a proper seal) of an end of the main endograft provided with such snorkels. The branch vessel grafts (snorkels) interfere with apposition of the main endograft to the blood vessel wall in the seal zone, leading to gutters alongside the snorkel that could allow continued pressurization of the diseased segment. This is best seen in FIG. 2B. Indeed, even attempts to overinflate or oversize a conventional circular/cylindrical endograft to force it to wrap around the smaller snorkel endografts have shown that undesirable gutters remain.

There is accordingly identified a need in the art for an endoluminal graft for use in parallel endograft techniques which, while effective for its intended purpose, provides additional advantages in preventing "gutters" alongside the ancillary or snorkel endografts, providing a good occlusive seal of the main endograft with a blood vessel wall and preventing blood leakage and potentially continued pressurization of the blood vessel lesion.

SUMMARY OF THE INVENTION

In accordance with the foregoing need identified in the art as described herein, a "snorkel" or "chimney" endoluminal graft or endograft, intended for use as an ancillary endograft to a substantially conventional main endograft for treating blood vessel wall lesions adjacent to branching blood vessels, is provided. Broadly, the described snorkel endograft includes at least a portion which does not define or can be made not to define a circular cross-sectional dimension. When used in parallel with other endografts such as at least one main endograft (defining a substantially circular cross-sectional dimension) and other like snorkel endografts, apposition of the endografts to each other and the blood vessel wall is facilitated to achieve an adequate seal for exclusion of pressure from the treated pathology.

In one aspect, the disclosure relates to an endograft wherein at least a portion thereof defines or can be made to define a cross-sectional dimension wherein a first surface of the snorkel endograft substantially conforms to a shape of an outer surface of a main endograft, and a second surface of the snorkel substantially conforms to a shape of an inner luminal surface of the blood vessel being treated. In embodiments, the disclosed snorkel endograft may define a variety of cross-sectional shapes, including without limitation an oblong, a lens, a crescent, a circular segment, and the like.

In the following description there are shown and described several different embodiments of this invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Figure 1A:
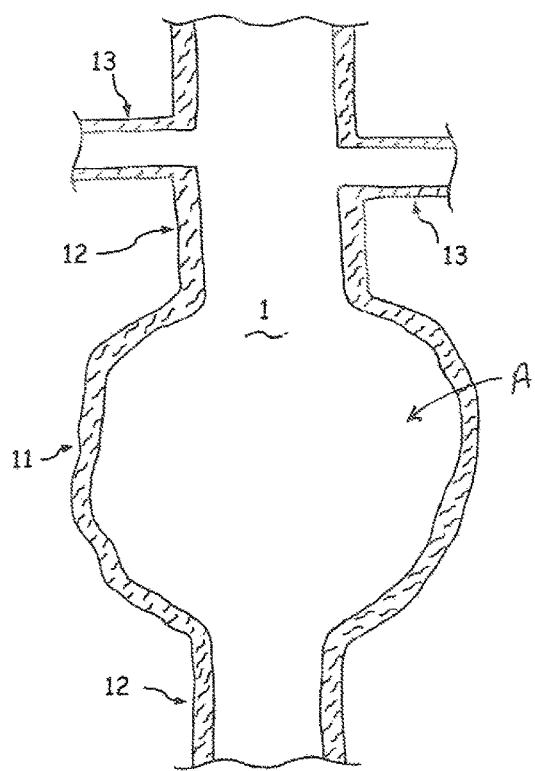
FIG. 1A shows a blood vessel (1) with a diseased aneurysmal segment (11) as well as healthy segments (12) proximal and distal to the aneurysmal segment (11) that can serve as seal zones for endoluminal repair of the aneurysm.
Figure 1B:
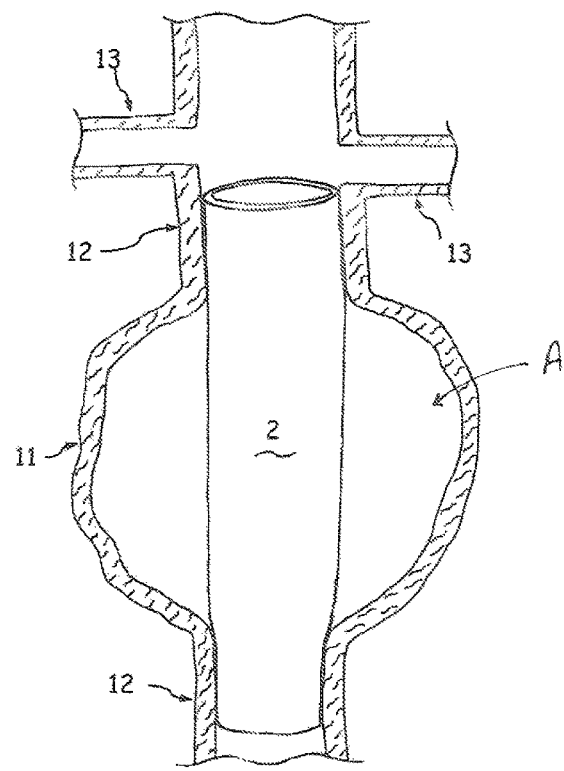
Figures 2A, 2B:
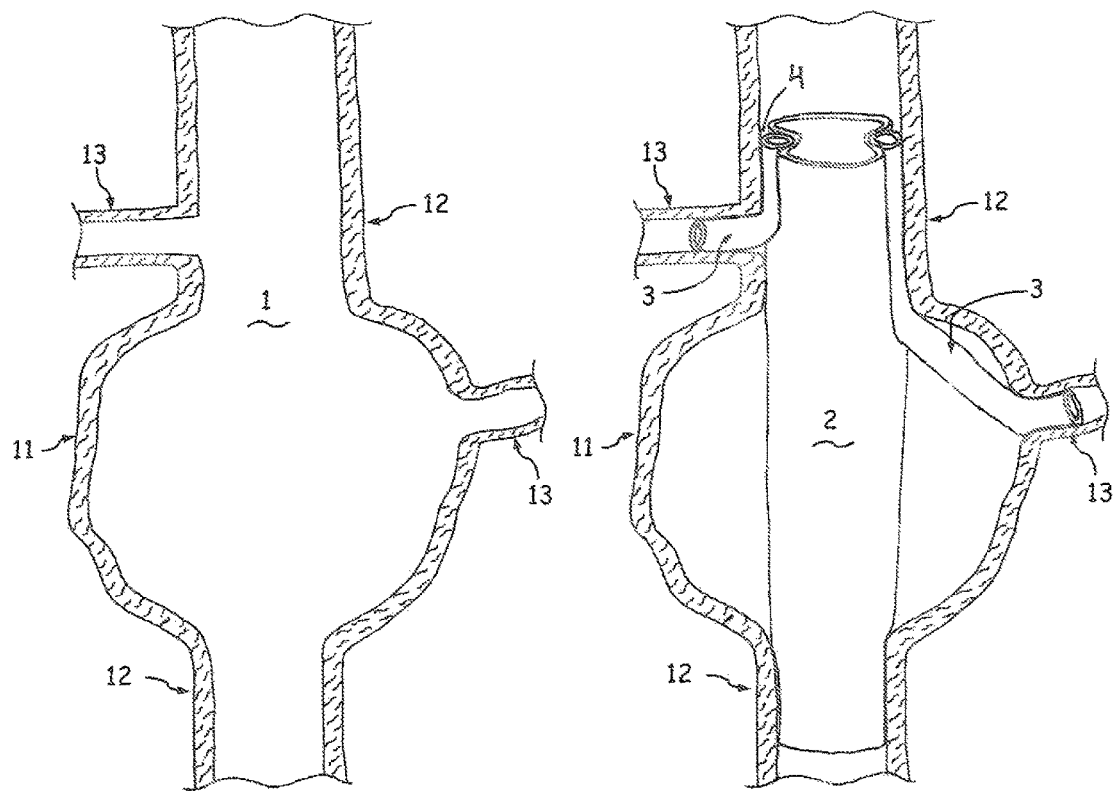
Figure 3A:
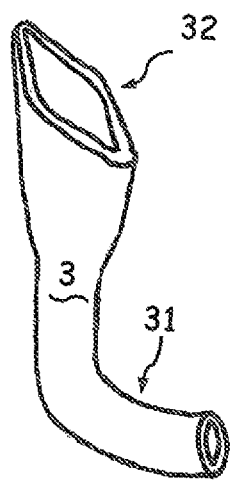
Figure 3B:
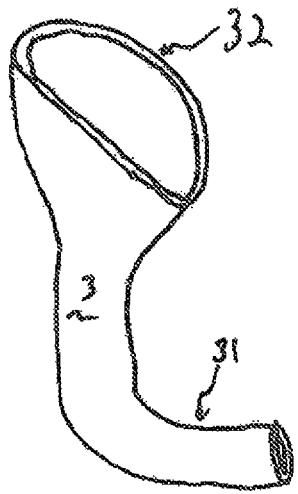
Figure 3C:
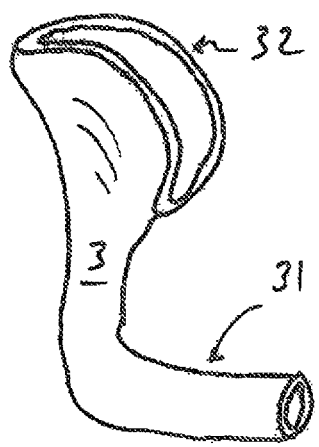
Figure 3D:
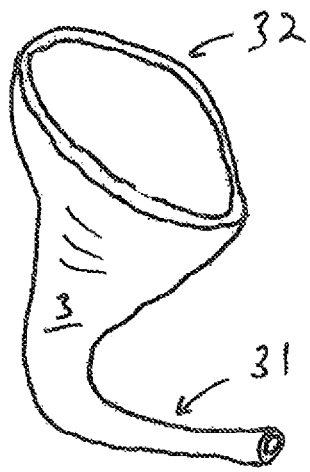
Figure 4A:
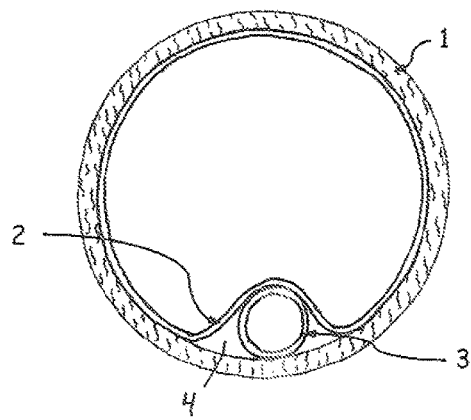
Figure 4B:
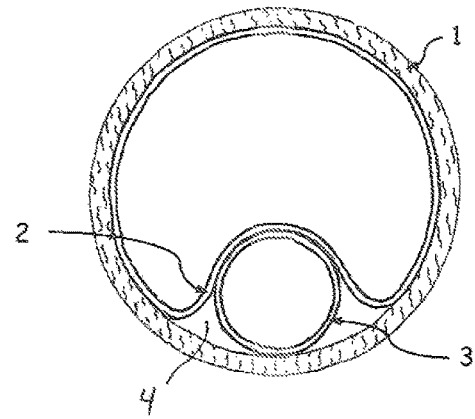
Figure 4C:
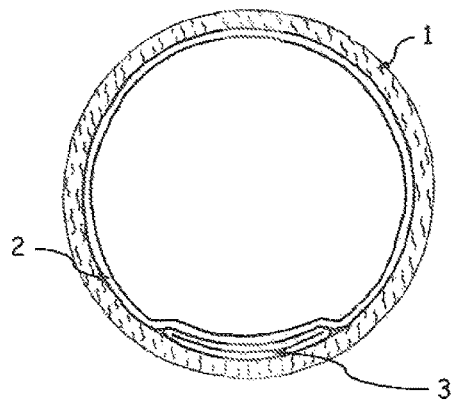
Figure 4D:
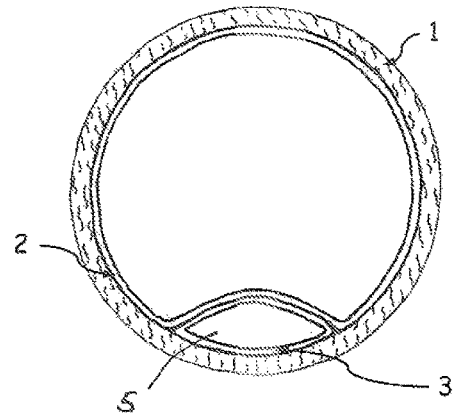
Figure 5:
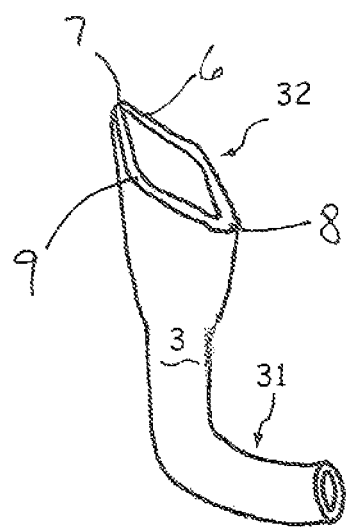

In this case, the branch vessels (13) arise outside of the necessary seal zone for endoluminal repair;

FIG. 1B shows the blood vessel of FIG. 1A with an appropriately placed stent graft or endograft (2) positioned, sized, and expanded so that its outer surface is apposed to the inner luminal surface of the blood vessel (1) in the seal zones (12) to exclude the systemic blood pressure from the aneurysmal segment (11);

FIG. 2A shows a blood vessel (1) with a diseased aneurysmal segment (11) as well as healthy segments (12) proximal and distal to the aneurysmal segment (11), with branch blood vessels (13) adjacent or inside the necessary seal zone (12) or from the aneurysmal segment (11);

FIG. 2B shows the blood vessel of FIG. 2A including smaller conventional "snorkel" or "chimney" stent grafts or endografts (3) placed alongside the main stent graft (2) and extending into the branch vessels (13). These smaller stent grafts (3) allow preservation of flow into the branch vessels (13) that would otherwise need to be sacrificed for standard endovascular repair in vessels with similar anatomy. However, they can also interfere with the apposition of the outer surface of the main stent graft (2) to the inner luminal surface of the blood vessel (1) creating an imperfect seal and potential continued pressurization of the aneurysmal segment (11). In the art, these parallel stent grafts are often referred to as "snorkel" or "chimney" grafts;

FIGS. 3A-D illustrate a stent graft or endograft 3 having a plurality of cross-sectional shapes at a portion thereof, with that portion defining convex vertices (FIG. 3A), a semi-circular shape (FIG. 3B), a crescent (FIG. 3C), and an ellipse (FIG. 3D). In each instance, the proximal portion assumes a partially flattened oblong shape (32) that is less likely to interfere with seal when placed in parallel to another endograft. The distal portion maintains the standard circular shape for apposition to the lumen of a branch vessel;

FIG. 4A shows a cross-sectional view of a blood vessel (1) with a main stent graft (2) and a smaller "snorkel" stent graft (3) placed in parallel, illustrating how the standard circular cross-sectional shape of the stent grafts, despite some conformation, results in an imperfect seal to the inner lumen of the blood vessel (1);

FIG. 4B shows the same cross-sectional view with the smaller "snorkel" stent graft (3) over-expanded using standard methods such as an intraluminal balloon;

FIG. 4C shows the same cross-sectional view with the "snorkel" stent graft (3) completely flattened using standard methods such as a balloon placed in the main stent graft (2). At this point, there is complete apposition of the two stent grafts to each other and to the luminal surface of the blood vessel (1);

FIG. 4D shows the same cross-sectional view after the "snorkel" stent graft (3) has been partially re-expanded using standard methods such as a smaller intraluminal balloon or stent. Note that this will now allow flow through the "snorkel" stent graft (3), while still maintaining full apposition of main stent graft (2) and the "snorkel" stent graft (3) to each other and the luminal surface of the blood vessel (1); and FIG. 5 shows the snorkel stent graft (3) of FIG. 3A in isolation.

Reference will now be made in detail to the present preferred embodiments of the invention, examples of which are illustrated in the accompanying drawings.

DETAILED DESCRIPTION OF THE INVENTION

A typical endoluminal graft is cylindrical in shape or round in cross section. This shape matches that of an interior luminal wall of a blood vessel 1. When a single, appropriately-sized endograft 2 is properly deployed in a vessel, there will be apposition of the outer surface of the endograft 1 to the inner surface of the vessel 1, creating a seal. However, when multiple conventional cylindrical endografts 1, 2 are deployed side by side within one cylindrical vessel, there will be gaps or "gutters" 4 in the seal due to limitations in the conformability of the endografts 1, 2 and imperfect apposition. This is illustrated in FIGS. 2B and 4A.

In accordance with the foregoing need identified in the art to correct the imperfect apposition inherent to multiple parallel endografts, an endoluminal graft 3 including at least a portion which may define a plurality of cross-sectional shapes other than a traditional circular cross-section (see FIGS. 3A-3D) is disclosed for use as a "snorkel" endograft 3. The plurality of cross-sectional shapes are independent of shape variation from conformational changes or constructed branch points. Typically, at least the portion of the snorkel endograft 3 which is to be deployed in parallel to a main, conventional endograft 2 (having a circular cross-section) will be provided with a non-circular cross-sectional dimension. By this non-circular cross-sectional dimension, the larger main endograft 2 can more easily conform with both the snorkel endograft 3 and the blood vessel 1 luminal wall 11 to appose the remaining surfaces and create a seal. Particular, though non-limiting, embodiments of a snorkel endograft 3 according to the present disclosure are shown in FIG. 3 and include without limitation an oblong shape with curved segments defining convex vertices (FIG. 3A), a circular segment (FIG. 3B), a crescent (FIG. 3C), and an ellipse (FIG. 3D).

In the embodiment of FIG. 3A, a substantially prolate sphere cross-sectional dimension is defined along at least a portion of the snorkel endograft 3, i.e. an oblong defining convex vertices. The defined cross-sectional dimension includes distinguishable segments and vertices (points of intersection) of such segments. With reference to FIG. 5, the referenced snorkel endograft 3 includes an outer segment 6 defining a curve substantially matching an arc of an inner luminal surface of the vessel (not shown in this view) where it is to be apposed. This segment 6 is bound on either end by a convex vertex 7, 8 forming an acute angle with a curved inner segment 9. The precise shape of this inner segment 9 is of lesser concern. Rather, it is the acuity of the angle of the vertices 7, 8 that lessens the conformational changes required of the main endograft 2 to appose the remaining luminal surface 11 of the blood vessel 1. Together, the snorkel endograft 3 outer and inner segments 7, 9 and their vertices 7, 8 create a cross-sectional shape resembling that of an eye or football, i.e. a prolate or oblate sphere in a two-dimensional view. Alternative shapes for the described distinguishable segments are of course contemplated, including without limitation crescents, circular segments, and the like as shown in FIG. 3.

A variety of methods of fabricating or providing snorkel endografts 3 having the desired non-circular portion according to the present disclosure are contemplated, including incorporating appropriately-shaped scaffolding in the construction of the endografts 3 whereby the endografts will assume the desired cross-sectional shape on deployment and/or inflation by balloon. Still more, shape memory alloys may be incorporated for constructing such scaffolding or other structural support for the endografts 3 whereby the endografts will automatically assume the desired cross-sectional shape on application of a suitable stimulus such as temperature or an electrical stimulus, as is known for shape memory alloys.

In another aspect, a method is provided for altering a cross-sectional shape of a portion of a conventional cylindrically shaped snorkel endograft 3 to provide a snorkel according to the present disclosure. The parallel portion of the snorkel 3 may be overdilated (see FIG. 4B) by an intraluminal force such as a large diameter balloon (not shown) placed inside the snorkel 3. The large diameter balloon is then exchanged for a smaller balloon and/or an intraluminal stent (not shown). Next, the snorkel 3 is crushed by inflating a large balloon (not shown) placed in the main endograft 2, effectively flattening the snorkel 3 and allowing full apposition of the endografts 2, 3 to the blood vessel 1 lumen and each other (see FIG. 4C). Finally, the smaller balloon in the flattened snorkel 3 is inflated to re-expand only the central portion 5 thereof, creating a suitable cross-sectional shape to fill the potential gaps of apposition, provide an occlusive seal, and prevent undesirable gutters 4.

The foregoing description of preferred embodiments has been presented for purposes of illustration and description. It is not intended to be exhaustive or limiting to the invention to the precise forms disclosed. Obvious modifications or variations are possible in light of the above teachings. The embodiments were chosen and described to provide the best illustration of the principles described herein and their practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A modular endograft system for deploying in a lumen, comprising:
    at least two endografts for disposing alongside or parallel one to another and contacting one another for at least a portion of a longitudinal dimension thereof, at least said parallel portion of a first of the at least two endografts defining or being made to define a non-circular cross-sectional configuration including a surface having a shape substantially conforming to a shape of an inner surface of said lumen, and a second of the at least two endografts defining a substantially circular cross-sectional configuration;
    whereby upon deployment, outer surfaces of the at least two endografts conform to and are apposed one to another and to said inner surface of said lumen, creating an occlusive seal between the at least two endografts and the lumen.

2. The modular endograft system of claim 1, wherein the lumen is a blood vessel.

3. The modular endograft system of claim 1, wherein the lumen is a prosthetic device.

4. The modular endograft system of claim 1, wherein the non-circular cross-sectional configuration defines or is made to define a two-dimensional shape that is one of a lens, a crescent, and an ellipse.

5. The modular endograft system of claim 1, wherein the non-circular cross-sectional configuration comprises two segments joined at each end by first and second vertices, wherein said two segments form acute angles at said first and second vertices;
    further wherein at least one of said segments defines a shape substantially conforming to an arc defined by a segment of the inner surface of said lumen.

6. An endograft for a blood vessel having a branch extending from said blood vessel, comprising:
    a body defining a plurality of cross-sectional shapes along a longitudinal axis of said body that are independent of shape variation from conformational changes or constructed branch points;
        said body including at least a first portion along the longitudinal axis of the body defining or being made to define a non-circular cross-sectional configuration comprising at least two vertices connected by at least two arc-shaped side walls, said arc-shaped side walls forming acute angles at said at least two vertices, and a second portion along the longitudinal axis of the body defining a substantially circular cross-sectional configuration;
    wherein upon deployment with a second endograft with a substantially circular cross-sectional shape, the first portion of the endograft and the substantially circular cross-sectional shape of the second endograft are in contact with and apposed to one another and to an inner surface of the blood vessel, thereby creating an occlusive seal therebetween.

7. The endograft of claim 6, wherein said first portion defines a larger cross-sectional configuration than said second portion.

8. The endograft of claim 7, wherein said first portion is configured to be over-expanded and then at least partially collapsed to define said non-circular cross-sectional configuration.

9. The endograft of claim 6, wherein said first portion defines or is made to define a two dimensional shape that is one of a lens and a crescent.

10. A modular endograft system for deploying in a lumen, comprising:
    first and second endografts for disposing alongside or parallel one to another and in contact with one another for at least a portion of a longitudinal dimension thereof, wherein:
        the first endograft defines or is made to define a non-circular cross-sectional shape including two first sidewall sections meeting at two first vertices, said two first sidewall sections forming acute angles at said two first vertices within the portion of the first endograft parallel the second endograft, said portion of the first endograft parallel to the second endograft including a first surface having a shape substantially conforming to a shape of an inner surface of said lumen; and
        within the lumen, the second endograft defines or is made to define a cross-sectional shape including two second sidewall sections meeting at two second vertices, said two second sidewall sections forming obtuse angles at said two second vertices within a portion of the second endograft parallel to the first endograft, said portion of the second endograft parallel to the first endograft including a second surface having a shape substantially conforming to the shape of the inner surface of the lumen;
    whereby upon deployment, the first and second endografts conform to and are apposed one to another and to said inner surface of said lumen, thereby creating an occlusive seal between the first and second endografts and the lumen.

* * * * *